United States Patent [19]

Yanagida et al.

[11] Patent Number: 5,286,639

[45] Date of Patent: Feb. 15, 1994

[54] RECOMBINANT AVIPOXVIRUS

[75] Inventors: Noboru Yanagida, Kawasaki; Sakiko Saeki, Tokyo; Ryohei Ogawa; Kouichi Kamogawa, both of Yokohama; Yoshiyuki Hayashi, Kusatsu; Kazunari Sawaguchi, Shiga, all of Japan

[73] Assignee: Nippon Zeon Co., Ltd., Tokyo, Japan

[21] Appl. No.: 652,490

[22] Filed: Feb. 8, 1991

Related U.S. Application Data

[63] Continuation-in-part of Ser. No. 244,780, Sep. 15, 1988, abandoned.

[30] Foreign Application Priority Data

Sep. 16, 1987 [JP] Japan .................................. 62-231653

[51] Int. Cl.$^5$ .................. C12N 7/01; C12N 15/86; A61K 39/275; A61K 39/295
[52] U.S. Cl. ................................. 435/235.1; 424/89; 435/172.3; 435/320.1; 935/65
[58] Field of Search ........................ 424/89, 88, 93; 435/69.1, 69.3, 172.3, 235.1, 948; 536/27, 23.72; 530/396; 935/12, 32, 65

[56] References Cited

U.S. PATENT DOCUMENTS

4,603,112 7/1986 Paoletti ........................ 435/235.1

FOREIGN PATENT DOCUMENTS

| | | |
|---|---|---|
| 0227414 | 7/1987 | European Pat. Off. . |
| 0248416 | 9/1988 | European Pat. Off. . |
| WO86/00528 | 1/1986 | PCT Int'l Appl. . |
| WO88/02022 | 3/1988 | PCT Int'l Appl. . |
| 8903429 | 4/1989 | World Int. Prop. O. . |

OTHER PUBLICATIONS

Jorgensen, C.A. 107:169718d, "Cloning, nucleotide sequence, and expression the Newcastle disease virus hemagglutinin-neuraminidase glycoprotein gene" (1987).
Wemers, C.A. 108:125379k, "The hemagglutinin-neuraminidase (HN) gene of Newcastle disease virus strain Italien (ndv Italien): comparison with HNs of other strains and expression by a vacciniarecombinant" (1988).
Chakrabati et al., (1986) from "Vaccines 86, New Approaches in Immunology", Ed. F. Brown et al, Cold Spring Harbor Laboratory, p. 2-292.
Nawake DR 1918 Expts with a combined vaccine for poultry CAB Abstracts OV052-00649; OI050.
Boyle et al, *Virology* 156, 355 (1987).
Millar et al, *J. Gen Virol* 67, (1986).
Spriggs et al, *J. Virol.* 61, 3416 (1987).
Venkatesan et al, *Cell* 125, 805 (1981).
Tomley et al, *J. Gen Virol* 69, 1025 (1988).
Binns et al, *Nucl. Acids Res* 15, 6563 (1987).
Drillien et al, *Virology* 160, 203 (1987).
Cavanagh, D. 1988. *Avian Pathology* vol. 17, pp. 755-758.
Chambers et al., *J. gen. Virol.*, 67, 475 (1986).
Mackett *J. gen. Virol.* 67, 2067 (1986).
Carolson, *Avian Diseases*, 30, 25 (1985).
Boyle et al., *J. gen. Virol.*, 67, 1591 (1986).
Binns et al., *Israel J. of Vet. Med.*, 42, 124 (1986).
Report of the Houghton Poultry Research Station, 1983-1984, p. 50.
Report of the Houghton Poultry Research Station, 1984-1985, p. 52.
Umino, Y. et al. 1987. *Arch. Virol.* vol. 94 pp. 97-107.
Iorio, R. M. et al. 1984, J. Virol. vol. 51 pp. 445-451.
Jorgensen E. D. et al. Jan. 1987 Virology 156(1) 12-24.
Chambers, P. et al. Mar. 1986 J. General Virology 67(3) 475-486.
Wemers C D et al 1987 ( ) Arch Virol 97(1-2) 101-113.
Adine D. F. 1980 "A Pilot Study of the Potency of a Combined Newcastle Fowl Pox", Dialog Accession #542968.

*Primary Examiner*—Richard A. Schwartz
*Assistant Examiner*—Mary E. Mosher
*Attorney, Agent, or Firm*—Armstrong, Westerman, Hattori, McLeland & Naughton

[57] ABSTRACT

A recombinant Avipoxvirus having inserted all or a part of cDNA coding for Newcastle disease virus-derived *hemagglutinin neuraminidase* in a genome region non-essential to proliferation of Avipoxvirus is provided. The recombinant Avipoxvirus is utilizable as vaccine for fowl.

7 Claims, 13 Drawing Sheets

FIG. 2

□P□ : 7.5K PROMOTER

▨▨▨ : NDV-HN GENE

■■■ : FPV RECOMBINATION DNA REGION

FIG. 4A

HN GENE

```
         10         20         30         40         50         60         70
AGATGACCAA AGGGCGATAT ACGGGTAGAA CGGTCGGGGA GGCCGTCCCT CAATCGGGGAG TCGGGCCTCA 80         90        100        110                    126
CAATATCCGT TCTACCGCAT CACCAATAGC AGTCTTCAGT C ATG GAC CGC GCA GTT AGC
                                             MET Asp Arg Ala Val Ser 141                                                171
CAA GTT GCG CTA GAG AAT GAT GAA AGA GAG GCA AAG AAT ACA TGG CGC TTG GTA
Gln Val Ala Leu Glu Asn Asp Glu Arg Glu Ala Lys Asn Thr Trp Arg Leu Val 186             201                                 216                231
TTC CGG ATT GCA ATC CTA CTT TTA ACG GTA ACC TTA GCC ATC TCT GCA GCC
Phe Arg Ile Ala Ile Leu Leu Leu Thr Val Thr Leu Ala Ile Ser Ala Ala 245             261                      276                      291
GCC CTT GCA TAT AGT ATG GAG GCC AGC ACA CCT AGC GAT CTT GTG GGC ATA CCG
Ala Leu Ala Tyr Ser MET Glu Ala Ser Thr Pro Ser Asp Leu Val Gly Ile Pro 306                             321                 336
ACT GCG ATC TCT AGA ACA GAG GAA AAG ATT ACA TCT GCA CTC GGT TCC AAT CAA
Thr Ala Ile Ser Arg Thr Glu Glu Lys Ile Thr Ser Ala Leu Gly Ser Asn Gln 351                      366                      381                396
GAT GTA GAT AGG ATA TAT AAG CAG GTG GCC CTC GAA TCT CCA CTG GCA TTG
Asp Val Asp Arg Ile Tyr Lys Gln Val Ala Leu Glu Ser Pro Leu Ala Leu
```

FIG. 4B

```
         411                426                441
CTA AAC ACC GAA TCT ACA ATT ATG AAC GCA ATA AAG TCT CTC TCT TAT CAG ATC
Leu Asn Thr Glu Ser Thr Ile MET Asn Ala Ile Lys Ser Leu Ser Tyr Gln Ile
456                471                486                501
AAT GGG GCC GCA AAT AGC AGC GGG TGT GGG GCA CCT ATT CAT GAT CCA GAT TAT
Asn Gly Ala Ala Asn Ser Ser Gly Cys Gly Ala Pro Ile His Asp Pro Asp Tyr
         515                531                546                561
ATT GGA GGA ATA GGT ATA AAA GAA CTT ATT GTA GAT GAT GCT AGC GAC GTC ACA TCA
Ile Gly Gly Ile Gly Ile Lys Glu Leu Ile Val Asp Asp Ala Ser Asp Val Thr Ser
         576                591                606
TTC TAT CCC TCT GCG TTC CAA GAA CAC CTG AAC TTT ATC CCG GCG CCT ACT ACA
Phe Tyr Pro Ser Ala Phe Gln Glu His Leu Asn Phe Ile Pro Ala Pro Thr Thr
         621                636                651                666
GGA TCA GGT TGC ACT CGG ATA CCC TCA TTT GAC ATG AGC GCT ACC CAC TAC TGT
Gly Ser Gly Cys Thr Arg Ile Pro Ser Phe Asp MET Ser Ala Thr His Tyr Cys
         681                696                711
TAT ACT CAC AAT GTG ATA TTA TCT GGC TGC AGA GAT CAC TCG CAC TCA CAT CAG
Tyr Thr His Asn Val Ile Leu Ser Gly Cys Arg Asp His Ser His Ser His Gln
726                741                756                771
TAT TTA GCA CTT GGT GTG CTT CGG ACA TCT GCA ACA GGG AGG GTA TTC TTT TCC
Tyr Leu Ala Leu Gly Val Leu Arg Thr Ser Ala Thr Gly Arg Val Phe Phe Ser
```

FIG. 4C

```
        786
ACT CTG CGT TCC ATC AAT CTG GAT GAC ACC CAA AAT CGG AAG TCT TGC AGT GTG
Thr Leu Arg Ser Ile Asn Leu Asp Asp Thr Gln Asn Arg Lys Ser Cys Ser Val
                                801                         816         831

846                                 861                         876
AGT GCA ACC CCC TTG GGT TGT GAT ATG CTG TGC TCT AAA GTC ATA GAG ACT GAA
Ser Ala Thr Pro Leu Gly Cys Asp MET Leu Cys Ser Lys Val Ile Glu Thr Glu 891                         906                         921                         936
GAA GAG GAT TAT AAC TCA GCT ATC CCC ACG TCG ATG GTA CAT GGA AGG TTA GGG
Glu Glu Asp Tyr Asn Ser Ala Ile Pro Thr Ser MET Val His Gly Arg Leu Gly 951                         966                         981
TTC GAC GGC CAA TAC CAC GAG AAA GAC CTA GAT GTC ACA CTA TTC GAG GAC
Phe Asp Gly Gln Tyr His Glu Lys Asp Leu Asp Val Thr Leu Phe Glu Asp 996                         1011                        1026                        1041
TGG GTG GCA AAC TAC CCA GGA GTA GGG GGC TCT TTT ATT GAC AAC CGC GTA
Trp Val Ala Asn Tyr Pro Gly Val Gly Gly Ser Phe Ile Asp Asn Arg Val 1056                        1071                        1086                        1101
TGG TTC CCA GTT TAC GGA GGG CTA AAA CCC AAT TCG CCC AGT GAC ACC GCA CAA
Trp Phe Pro Val Tyr Gly Gly Leu Lys Pro Asn Ser Pro Ser Asp Thr Ala Gln 1116                        1131                        1146
GAA GGG AAA TAT GTA ATA TAC AAG CGA TAC AAT GAC ACA TGT CCA GAT GAG CAG
Glu Gly Lys Tyr Val Ile Tyr Lys Arg Tyr Asn Asp Thr Cys Pro Asp Glu Gln
```

FIG. 4D

```
                                    1176                          1191                         1206
1161
GAT TAT CAG ATT CGA ATG GCT AAG TCT TCA TAT AAG CCT GGG CGA TTT GGT GGG
Asp Tyr Gln Ile Arg MET Ala Lys Ser Ser Tyr Lys Pro Gly Arg Phe Gly Gly 1221                          1236                         1251
AAA CGA GTA CAG CAG GCC ATC TTA TCT ATC AAA GTG TCA ACA TCC TTG GGC GAG
Lys Arg Val Gln Gln Ala Ile Leu Ser Ile Lys Val Ser Thr Ser Leu Gly Glu 1266                        1281                          1296                         1311
GAC CCG GTG CTG ACT GTG CCG CCC AAC ACA GTC ACA CTC ATG GGG GCC GAA GGC
Asp Pro Val Leu Thr Val Pro Pro Asn Thr Val Thr Leu MET Gly Ala Glu Gly 1326                          1341                         1356                         1371
AGA GTT CTC ACA GTA GGG ACA TCT CAT TTC TTT TAT CAG CGA GGG TCG TCA TAC
Arg Val Leu Thr Val Gly Thr Ser His Phe Phe Tyr Gln Arg Gly Ser Ser Tyr 1386                         1401                         1416
TTC TCC CCT GCC CTA CTA TAT CCT ATG CCT ATG TTC ACT CGA GTC CCC TGC CAG
Phe Ser Pro Ala Leu Leu Tyr Pro MET Thr Val Ser Asn Lys Thr Ala Thr Leu
```

FIG. 4E

```
1536                          1551                       1566                        1581
CCC TTG GTC TTT TAT AGG AAC CAC ACC TTG CGA GGG GTA TTC GGG ACG ATG CTT
Pro Leu Val Phe Tyr Arg Asn His Thr Leu Arg Gly Val Phe Gly Thr MET Leu 1596                       1611                       1626                        1641
GAT GAT GAA CAA AGA CTT AAC CCT GTA TCT GCA GTA TTT GAC AGC ATA TCT
Asp Asp Glu Gln Ala Arg Leu Asn Pro Val Ser Ala Val Phe Asp Ser Ile Ser 1656                        1671                       1686
CGC AGT CGC ATA ACC CGG GTG AGT TCA AGC AGC AGC ACC AAG GCA TAC ACA ACA
Arg Ser Arg Ile Thr Arg Val Ser Ser Ser Ser Ser Thr Lys Ala Tyr Thr Thr 1701                       1716                       1731                        1746
TCA ACA TGT TTT AAA GTT GTA AAG ACC AAT AAG ACA TAT TGT CTC AGC ATT GCC
Ser Thr Cys Phe Lys Val Val Lys Thr Asn Lys Thr Tyr Cys Leu Ser Ile Ala 1761                       1776                        1791
GAA ATA TCC AAT ACC CTC TTC GGG GAA TTC AGA ATC GTC CCT TTA CTA GTT GAG
Glu Ile Ser Asn Thr Leu Phe Gly Glu Phe Arg Ile Val Pro Leu Leu Val Glu 1806                        1821                       1835                        1851
ATT CTC AAG GAT GAT ATT GGG GTT AGA GAA GCC AGG TCT GGC CGG TTG AGT CAA TTG
Ile Leu Lys Asp Asp Ile Gly Val Arg Glu Ala Arg Ser Gly Arg Leu Ser Gln Leu

*              1866                       1881                       1896                        1911
CAA GAG GGT TGG AAA GAT ATT GTA TCG CCT ATC TTT TGC GAC GCC AAG AAT
Gln Glu Gly Trp Lys Asp Ile Val Ser Pro Ile Phe Cys Asp Ala Lys Asn 1926                       1941                       1956                        1972
CAA ACT GAG TAC CGG CGC GAG CTC GAG CTC TAC GCT GCC AGC TGG CCA TAA TCAGCTAGTG
Gln Thr Glu Tyr Arg Arg Glu Leu Glu Leu Tyr Ala Ala Ser Trp Pro 1982       1992
CTAATGTGAT TAGATTAAGT CTCGTCGA
```

E : EcoRI   P : PstI   G : BglII
X : XbaI    B : BamHI
V : EcoRV   H : HindIII
Hc : HincII C : ClaI
K : KpnI    Xb : XbaI
            Hp : HpaI

RECOMBINANT AVIPOXVIRUS

This application is a continuation-in-part of application Ser. No. 244,780, filed Sept. 15, 1988, now abandoned.

FIELD OF THE INVENTION AND RELATED ART STATEMENT

1. Field of the Invention

The present invention relates to a recombinant Avipoxvirus and more particularly, to a recombinant Avipoxvirus having inserted Newcastle disease-derived cDNA into a DNA region non-essential to proliferation of Avipoxvirus.

2. Related Art

In recent years, a method of constructing recombinant vaccinia virus having inserted Newcastle disease virus-derived cDNA into vaccinia virus has been devised and there has been come to propose a method utilizing recombinant vaccinia virus obtained using, as exogenous DNA, for example, DNA coding for infectious diseases as live vaccine (for example, Published Unexamined Japanese Patent Application KOKAI No. 129971/83, Public Disclosure Nos. 500518/85, 501957/86, etc.). According to this method, it is possible to insert a variety of exogenous DNAs depending upon purpose and, the method is expected to be promising as a new process for producing live vaccine.

In vaccinia virus, however, its host range is limited. For this reason, it is almost impossible to apply techniques of recombinant vaccinia virus to production of, for example, live vaccine against chick disease such as Newcastle disease and for the purpose of producing avian live vaccine, a suggested promising method is to insert exogenous DNA into Fowlpoxvirus in lieu of vaccinia virus (Avian Disease, , vol. 30, No. 1, 24–27). However, comparing vaccinia virus and Fowlpoxvirus, they belong to different genera; the former belonging to the genus Poxvirus and the latter to the genus Avipoxvirus. Further, there is a difference in a length of genome by about 1.5 times because the former has a genome length of about 180 Kb and the latter has a genome length of 260 to 270 Kb. Furthermore, with vaccinia virus, its genome DNA structure has been clarified to a remarkable extent, but only restriction enzyme cleavage pattern of genome DNA is known with Fowlpoxvirus (J. Gen. Virol., 38, 135–147 (1977)); turning to function of genome DNA, the presence of thymidine kinase gene is merely proved [J. Gen. Virol., 67, 1591–1600 (1986)].

Accordingly, it is expected that application of the aforesaid method of constructing recombinant vaccinia virus to Avipoxvirus would be accompanied by many difficulties. For this reason, there has recently been found cDNA coding for hemagglutinin neuraminidase (HN) and/or F polypeptide of Newcastle disease virus [for example, J. Gen. Virol., 67, 1917–1927 (1986), Published Unexamined Japanese Patent Application KOKAI No. 163693/87]. However, any recombinant Avipoxvirus having inserted such cDNA thereon has not yet been obtained.

SUMMARY OF THE INVENTION

Therefore, the present inventors have made extensive investigations under the state of the art, aiming at construction of a recombinant Avipoxvirus capable of proliferation in which cDNA coding for an antigen derived from Newcastle disease virus (hereafter sometimes referred to as NDV) has been inserted into genome DNA. As a result, the present inventors have found that the recombinant Avipoxvirus capable of proliferation can be obtained by selecting a hemagglutinin neuraminidase (hereafter sometimes referred to as HN)-coding region from NDV cDNA and inserting the region into a genome region non-essential to proliferation of Avipoxvirus and have come to accomplish the present invention.

Thus, according to the present invention, there is provided a recombinant Avipoxvirus in which NDV-derived antigen-encoding cDNA has been inserted into a genome region non-essential to proliferation of Avipoxvirus, preferably together with DNA having a promoter function, in the form capable of expression.

BRIEF DESCRIPTION OF THE DRAWINGS

FIGS. 1, 2 and 3A–B show procedures for construction of recombinant Avipoxvirus. FIG. 4A–E shows an amino acid sequence and base sequence of HN gene from NDV. FIG. 6 illustrates procedures for construction of hybrid plasmid (A) referred to in the present invention.

DETAILED DESCRIPTION OF THE PREFERRED EMBODIMENTS

Figure 1:
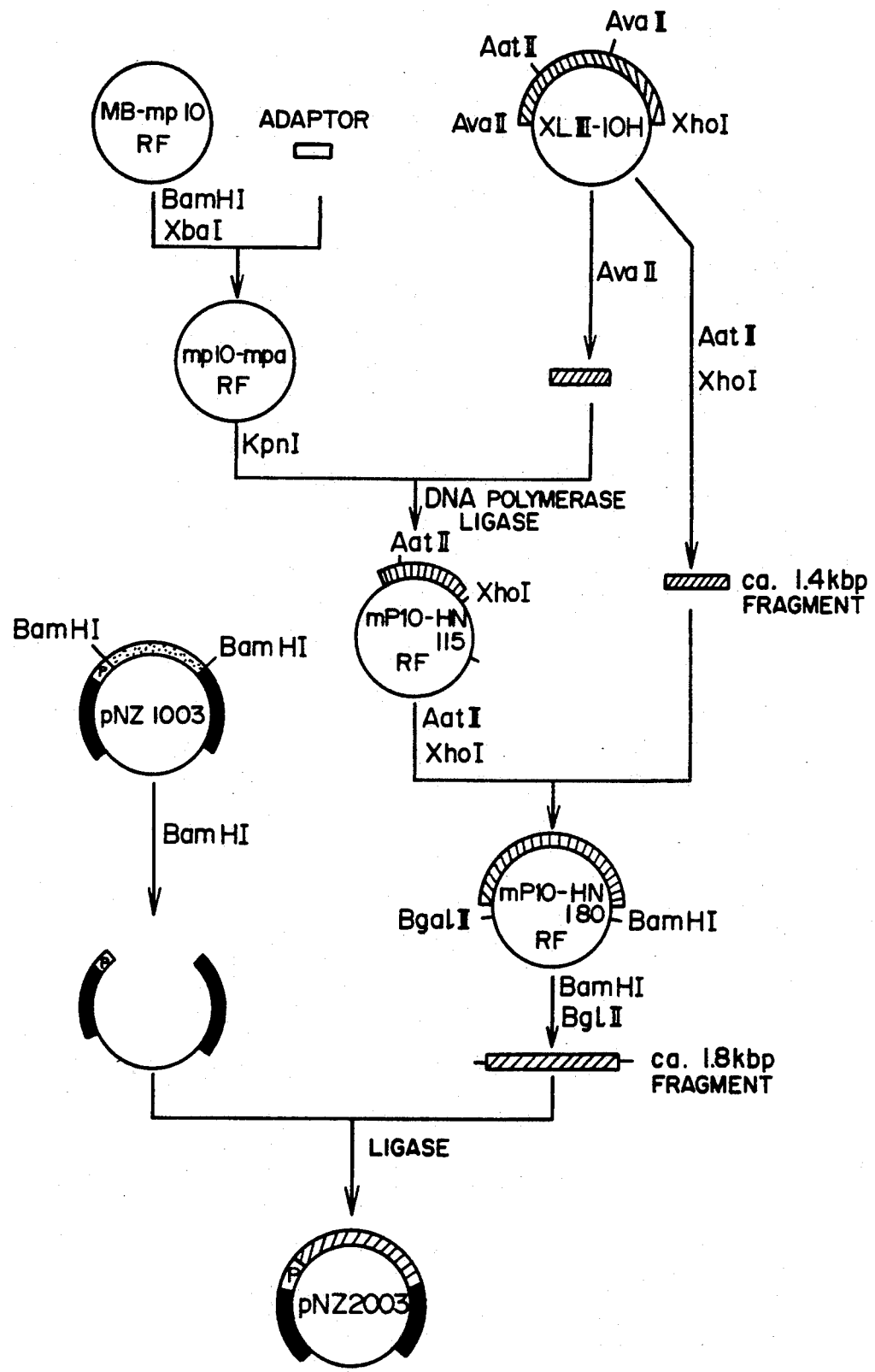

Any virus is usable as the virus employed to insert NDV-derived cDNA in the present invention as far as it is classified into the genus Avipoxvirus but preferred are those capable of growing in cells of fowls such as chicken, turkey, duck, etc. Specific examples include Fowlpoxvirus such as ATCC VR-251, ATCC VR-250, ATCC VR-229, ATCC VR-249, ATCC VR-288, Nishigawara strain, Shisui strain, etc.; and those akin to Fowlpoxvirus and used to avian live vaccine strain such as NP strain (chick embryo habituated dovepoxvirus Nakano strain), etc. These strains are all commercially available and easily accessible.

Further, cDNA coding for NDV-derived HN can be prepared using, for example, D-26 strain of NDV or Beaudette C strain. cDNA prepared from, for example, D-26 strain described above includes two kinds, one of which is composed of 1746 base pairs from 112th to 1857th and another is composed of 1848 base pairs from 112th to 1959th, among the base sequence shown in FIG. 4. A difference in both cDNAs lies in 1747th base in FIG. 4 (base marked with * in FIG. 4) wherein, in the case of long cDNA, the base is C as shown in the figure but is substituted on T in the case of short cDNA and thus constitutes a translation termination codon (TAA). For information, cDNA used in the examples is short one.

Further cDNA prepared from Beaudette C strain is composed of 1731 base pairs [N. Miller, J. Gen. Virol., 67, 1917–1927 (1986)] and has a structure in which the base sequence are substituted at portions amounted to 170 in short cDNA prepared from D-26 strain.

As such, base sequences of cDNA encoding NDV-derived HN gene are not necessarily identical but in the present invention, cDNA may be modified one (namely, cDNA in which the base sequence is substituted, inserted or deleted), within such a range that cDNAs have substantially the same function as in the 3 kinds of cDNAs described above. Of course, insofar as they have substantially the same function, they may also be modified to such an extent that amino acid sequences are different.

Upon practice of the present invention, a first recombinant vector in which a DNA region non-essential to growth of Avipoxvirus has been inserted is firstly constructed. Preferred is a recombinant vector containing in the same region a promoter functioning in Avipoxvirus.

Specific examples of the DNA region non-essential to growth include regions which cause homologous recombination with EcoR I-Hind III fragment (about 5.0 kbp), BamH I fragment (about 4.0 Kbp), EcoR V-Hind III fragment (about 1.8 kbp), BamH I fragment (about 3.3 Kbp), Hind III fragment (about 5.2 Kbp), etc.

Such a DNA region non-essential to growth can be fixed, for example, by the following procedures. First, hybrid plasmid (A) having inserted therein an optional DNA fragment from Avipoxvirus genome and hybrid plasmid (B) having ligated DNA encoding an enzyme capable of being readily detected under control of a promoter are prepared. Next, a DNA fragment fully containing DNA coding for the promoter and the enzyme is prepared from hybrid plasmid (B). By inserting the DNA fragment into a virus DNA portion of hybrid plasmid (A), hybrid plasmid (C) is prepared. Then, hybrid plasmid (C) is transfected into a host cell previously infected with Avipoxvirus, whereby positive or negative formation of recombinant Avipoxvirus is confirmed.

Selection for examining as to if a recombinant Avipoxvirus is constructed by a series of procedures described above may be performed in a conventional manner. Where, for example, $\beta$-galactosidase gene is used as enzyme-coding DNA, agarose medium containing chlorophenol red-$\beta$-D-galactopyranoside (CPRG) is overlaid in layers after plaques are recognized on a medium for forming plaques of recombinant Avipoxvirus; plaques stained red by incubation at 37° C. may thus be selected.

As such, in case that a recombinant Avipoxvirus is obtained using detection of enzyme activity as a means for selection, it is indicated that an Avipoxvirus-derived DNA fragment used for construction of hybrid plasmid (A) is a DNA region non-essential to growth.

The DNA having a promoter function as used in the present invention may be any DNA having any base sequence as long as it can effectively function as a promoter in the transcription system possessed by Avipoxvirus, irrespective of synthesized or naturally occurring DNA. Needless to say, promoters intrinsic to Avipoxvirus such as a promoter of Avipoxvirus gene coding for thymidine kinase are usable and, even DNA derived from virus other than Avipoxvirus or DNA derived from eucaryote or procaryote can be naturally used in the present invention, as far as it meets the requirement described above.

Concrete examples of these promoters include promoters of vaccinia virus illustrated in Journal of Virology, September 1984, 662–669, specifically, a promoter of vaccinia virus gene coding for 7.5K polypeptide, a promoter of vaccinia virus gene coding for 19K polypeptide, a promoter of vaccinia virus gene coding for 42K polypeptide, a promoter of vaccinia virus gene coding for thymidine kinase polypeptide, a promoter of vaccinia virus gene coding for 28K polypeptide, etc. The promoter may be complete or partly modified as long as it retains the function.

A first recombinant vector may be constructed in a conventional manner. For example, after inserting a DNA fragment non-essential to growth of Avipoxvirus into an appropriate vector, a promoter added with a restriction enzyme cleavage sequence may be incorporated at the downstream thereof, if necessary and desired, utilizing restriction enzyme cleavage sites present in the fragment.

Specific examples of the vector used herein include a plasmid such as pBR 322, pBR 325, pBR 327, pBR 328, pUC 7, pUC 8, pUC 9, pUC 19, etc.; a phage such as ! phage, M13 phage, etc.; a cosmid such as pHC 79 (Gene, 11, 291, 1980) and the like.

In the present invention, a second recombinant vector is constructed by inserting a NDV HN-coding region into the promoter of the first recombinant vector at the downstream thereof. Insertion may also be effected in a conventional manner. For example, NDV-derived cDNA fragment may be inserted, utilizing a restriction enzyme cleavage site previously provided at the downstream of the promoter of the first vector.

Upon construction of these first and second recombinant vectors, the *Escherichia coli* system in which genetic manipulations are easy may be used. The plasmid vector used is not particularly limited as far as it is suited for purposes.

In the present invention, next, the second recombinant vector is transfected into animal culture cells previously infected with Avipoxvirus to cause homologous recombination between the vector DNA and the virus genome DNA, whereby a recombinant Avipoxvirus is constructed. The animal culture cells as used herein may be any cells insofar as Avipoxvirus can grow there. Specific examples are chick-derived culture cells such as chick embryo fibroblasts, etc. Furthermore, chick chorioallantoic membrane is also naturally included in the category of host cell.

Construction of the recombinant Avipoxvirus may be carried out in a conventional manner. The second recombinant vector treated by the calcium phosphate coprecipitation method is transfected into host cells infected with Avipoxvirus according to, for example, D. M. Glover, DNA Cloning, volume II, a practical approach, pp. 191–211, IRL Press, Oxford, Wash. The thus obtained virus mass containing a recombinant virus is infected to host cells cultured on Eagle's MEM medium. Plaques grown on the medium may be made recombinant virus candidate strains. For selection of a virus having inserted therein a DNA fragment coding for NDV HN from these candidate strains, the candidate strains may be purified by a hybridization method using the DNA as a probe and immunoassay using an NDV antibody is then applied.

Therefore, according to the present invention, there is provided the recombinant Avipoxvirus which is utilizable as a live vaccine for fowls and in which NDV-derived antigen-coding cDNA has been inserted into a genome region non-essential to proliferation of Avipoxvirus, together with a DNA having promoter functions, in the form capable of expression.

The present invention will be described in more detail with reference to the examples and the reference examples below. Reference Example 1 (identification of nonessential DNA region)

(1) Construction of Avipoxvirus genome DNA

Avipoxvirus NP strain (chick embryo habituated dovepoxvirus Nakano strain, manufactured by Japan Pharmacy Co., Ltd.) was inoculated on chick embryo fibloblasts cultured in a 75 cm² culture flask in 1 p.f.u./cell. After culturing in an incubator at 37° C. in 5% $CO_2$ for 2 hours, 15 ml of Eagle's MEM medium supplemented with 10% Tryptose phosphate broth (Difco Co., Ltd.) and 0.03% L-glutamine was added followed by incubation in an incubator for 4 days at 37° C. in 5% $CO_2$. Then the culture supernatant was centrifuged at 3000 r.p.m. for 10 minutes to recover the supernatant. The supernatant was centrifuged at 25000 r.p.m. (about 98000×g) for an hour and the precipitates were recovered. The precipitates were suspended in a DNase in a reaction buffer (50 mM Tris, pH 7.5, 1 mM $MgCl_2$) of a 1/10 volume of the culture supernatant and DNase I (Boehringer Mannheim Co., Ltd.) was added to the suspension in 9 μ/ml followed by reacting at 37° C. for 30 minutes. After the reaction, 25 mM EDTA.2Na was added and the mixture was allowed to stand at room temperature for 30 minutes. Thereafter, 500 μg/ml of proteinase K (Boehringer Mannheim Co., Ltd.) and sodium dodecyl sulfate (SDS) were added to the mixture in a 1% concentration followed by reacting at 37° C. overnight. After gently treating with phenol-chloroform, the reaction mixture was precipitated with ethanol to give 0.5 μg of virus DNA.

Figure 6:
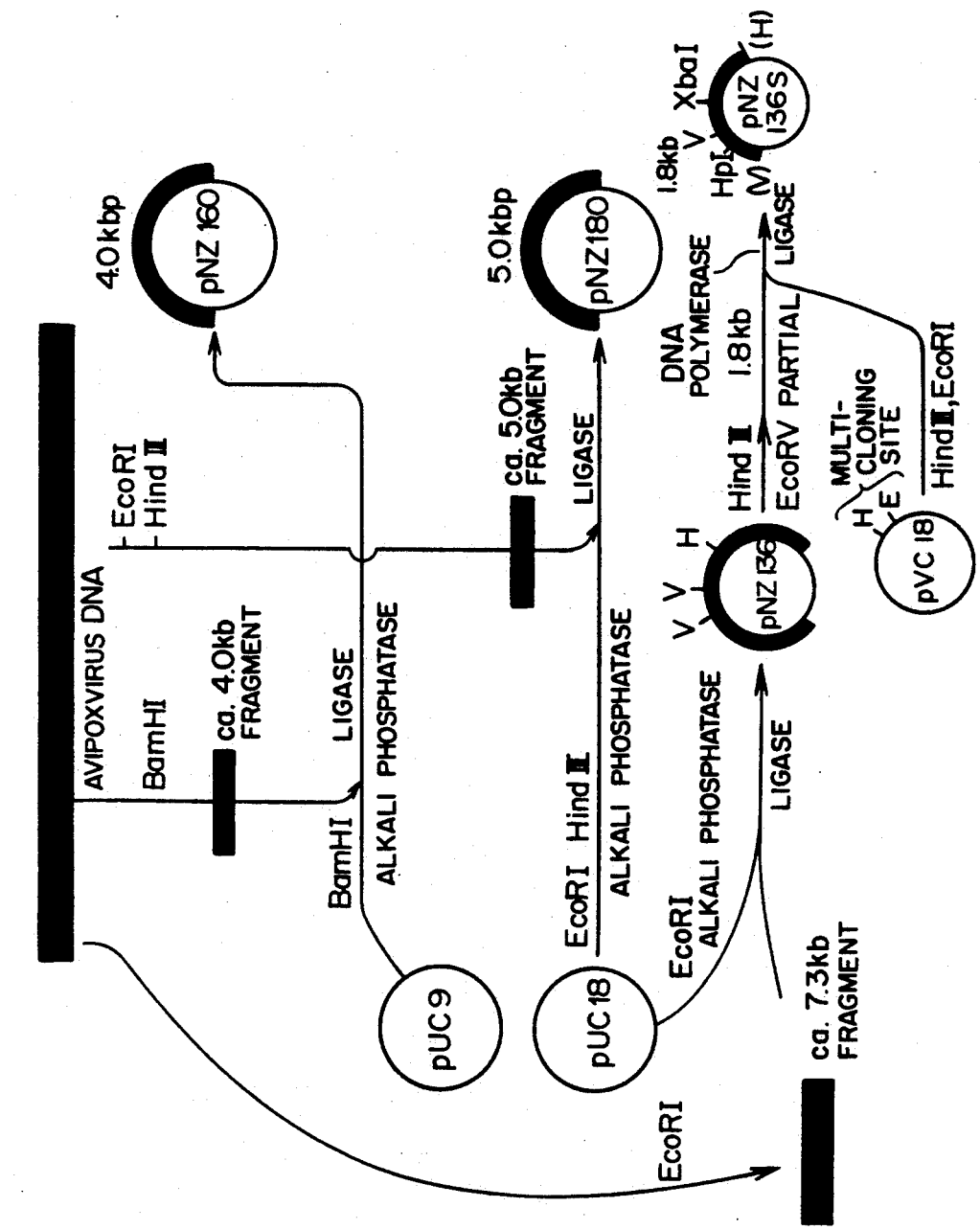
FIG. 6 shows a procedure for construction of a plasmid vector containing at least a part of the DNA region non-essential to proliferation.
Figure 7:
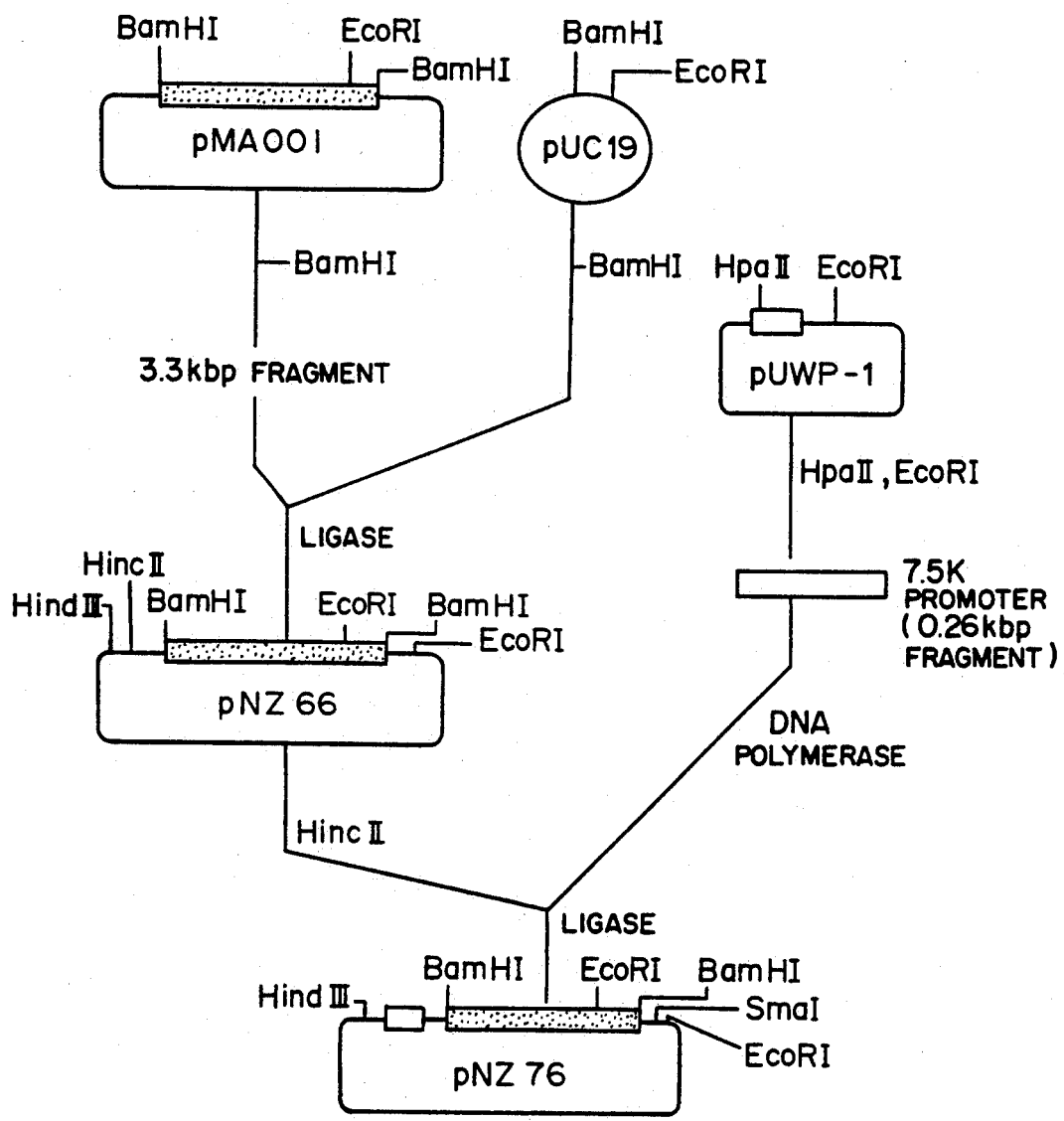
FIG. 7 illustrates procedures for construction of hybrid plasmid (B).

(2) Construction of hybrid plasmid (A) containing Avipoxvirus genome fragment (cf. FIG. 6)

Figure 8:
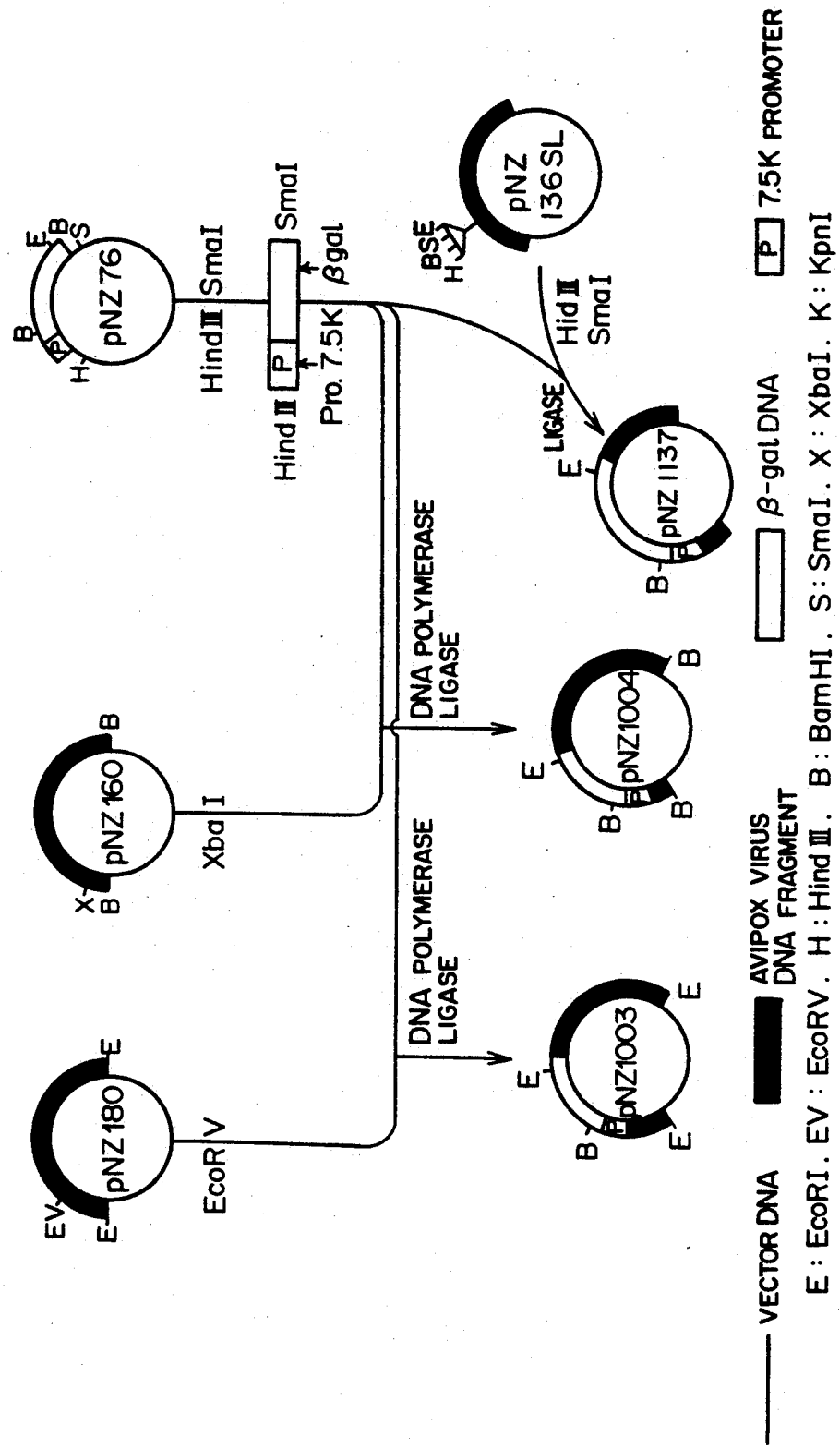
FIG. 8 illustrates procedures for construction of hybrid plasmid (C).

(a) Construction of plasmid (pNZ 180) containing about 5.0 Kb EcoR I-Hind III fragment of DNA of Avipoxvirus NP strain:

After digesting 2 μg of pUC 18 (manufactured by Pharmacia Inc.) with EcoR I and Hind III, extraction was performed with phenol-chloroform (1:1) to recover pUC 18 cleaved by precipitation with ethanol. 5'-End phosphate was removed by treating with alkali phosphatase. After extraction again with phenol-chloroform, DNA was recovered by precipitation with ethanol. The cleaved pUC 18, 0.2 μg, and the digestion product of 1 μg of purified Avipoxvirus (NP strain) DNA with EcoR I and Hind III were ligated with each other. Competent *E. coli* JM 103 was transformed and cultured at 37° C. for 15 hours in LB agar medium supplemented with 0.003% of 5-bromo-4-chloro-3-indolyl-β-D-galactopyranoside, 0.03 mM of isopropyl-β-D-galactopyranoside and 40 μg/ml of ampicillin. White colony out of the transformed *E. coli* grown on agar medium was cultured at 37° C. for 15 hours in LB liquid medium added with 40 μg/ml of ampicillin and plasmid was extracted by the method of Birnboim and Doly [Nucleic Acid Research, 7, 1513 (1979)]. After digesting with EcoR I and Hind IIID, a hybrid plasmid having a fragment of the same length as that of the original Avipoxvirus DNA EcoR I-Hind III fragment was detected by 0.6% agarose electrophoresis, which was named pNZ 180. A restriction enzyme map of the about 5.0Kb EcoR I-Hind III fragment is shown in FIG. 5(*a*). pNZ 180 corresponds to hybrid plasmid (A).

(b) Construction of plasmid (pNZ 160) containing about 4.0 Kb BamH I fragment of DNA from Avipoxvirus NP strain:

A hybrid plasmid was obtained in a manner similar to (a) except that vector pUC 18 used in (a) was changed to pUC 9 and about 4.0 Kb BamH I fragment of NP strain DNA was used in lieu of the EcoR I-Hind III fragment. This hybrid plasmid was named pNZ 160. A restriction enzyme map of about 4.0 Kb BamH I fragment is shown in FIG. 5(*b*) and pNZ 160 corresponds to hybrid plasmid (A). (c) Construction of plasmid (pNZ 136S) containing about 1.8 Kb EcoR V-Hind III fragment of DNA from Avipoxvirus NP strain:

A hybrid plasmid was obtained in a manner similar to (2) except that about 7.3 Kb EcoR I fragment of NP strain DNA was used in lieu of about 5.0 Kb EcoR I-Hind III fragment used in (2). This hybrid plasmid was named pNZ 136. Furthermore, after pNZ 136 was digested with Hind III, the digestion product was partially digested with EcoR V. The partial digestion product was subjected to 0.8% agarose electrophoresis to recover about 1.8 Kb EcoR V-Hind III fragment composed of about 0.6 Kb EcoR v-EcoR V fragment and about 1.2 Kb EcoR V-Hind III fragment adjacent to each other.

On the other hand, after pUC 18 was digested with Hind III and EcoR I, extraction was performed with phenol : chloroform (1:1) and the extract was precipitated with ethanol to recover cleaved pUC 18. The cleaved pUC 18 and about 1.8 Kb EcoR V-Hind III fragment recovered from agarose gel were blunted with DNA polymerase followed by ligation with ligase. Competent *E. coli* JM 103 was transformed and the transformants were selected on ampicillin-supplemented LB agar medium to give a plasmid containing about 1.8 Kb EcoR V-Hind III fragment. The plasmid was named pNZ 136S.

A restriction enzyme map of about 1.8 kb EcoR V-Hind III fragment is shown in FIG. 5(*e*) and pNZ 136S corresponds to hybrid plasmid (A).

(3) Construction of a second hybrid plasmid (B) (pNZ 76) ligated with a promoter and DNA coding for readily detectable enzyme under its control (cf. FIG. 7)

A plasmid having inserted about 0.26 kbp of Sal I-Rsa I fragment containing a promoter of DNA coding for 7.5K dalton peptide of vaccinia virus WR strain [Cell, 125, 805-813 (1981)] into Sal I-Sma I portion of pUC 9 was named pUWP-1.

After digesting 10 μg of pMA 001 [Shirakawa et al., Gene, 28, 127 (1984)]with BamH I, β-galactosidase gene (about 3.3 kbp) was recovered in a manner similar to (2). On the other hand, after digesting 0.3 μg of pUC 19 with BamH I, extraction was performed with phenol-chloroform and recovery was made through precipitation with ethanol. By ligation with the β-galactosidase gene prepared as described above, hybrid plasmid pNZ 66 was constructed.

On the other hand, 40 μg of pUWP-1 was digested with Hpa II and EcoR I and, a fragment of about 0.26 kbp containing 7.5K promoter was separated by 1.5% low melting point agarose electrophoresis (70 volts, 6 hours) and DNA was recovered by operation similar to (2). The cohesive end of this DNA fragment was made the blunt end by DNA polymerase. After 0.3 μg of pNZ 66 was digested with Hinc II, extraction was performed with phenol-chloroform and recovery was made through precipitation with ethanol. By ligation with about 0.26 kbp of the 7.5K promoter gene described above, a hybrid plasmid was obtained and named pNZ 76. pNZ 76 corresponds to hybrid plasmid (B).

(4) Construction of hybrid plasmid (C) from hybrid plasmid (A) and hybrid plasmid (B) (cf. FIG. 8)

(a) Construction of hybrid plasmid (pNZ 1003) having inserted a ligation fragment of vaccinia virus 7.5K promoter and β-galactosidase DNA into EcoR V site of pNZ 180

After digesting 10 μg of pNZ 76 with Hind III and Sma I, a fragment of about 3.6 kbp was separated by 0.7% low melting point agarose electrophoresis (40 volts, 20 hours). After the DNA fragment was confirmed by staining with ethidium bromide, gel was excised, treated with phenol and precipitated with ethanol to recover the DNA fragment.

On the other hand, 1 μg of pNZ 180 was digested with EcoR V, extracted with phenol-chloroform and precipitated with ethanol to recover the same. The cleaved pNZ 180 DNA, 0.3 μg, was mixed with about 0.4 μg of the aforesaid about 3.6 kbp fragment (ligation fragment of 7.5K promoter DNA and β-galactosidase gene) and the cohesive end was made the blunt end by DNA polymerase. After extracting with phenol-chloroform, the DNA was recovered. The recovered DNA was ligated with ligase. Competent E. coli JM 103 strain was transformed and allowed to grow at 37° C. for 15 hours in LB agar medium supplemented with 40 μg/ml of ampicillin. A plasmid was recovered from E. coli grown in a manner similar to (2) and digested with BamH I. A hybrid plasmid containing a β-galactosidase gene fragment (about 3.3 kbp) was selected by 0.5% agarose electrophoresis, which was named pNZ 1003.

(b) Construction of hybrid plasmid (pNZ 1004) having inserted a ligation fragment of vaccinia virus 7.5K promoter and β-galactosidase DNA into Xba I site of pNZ 160

A hybrid plasmid containing a β-galactosidase gene fragment (about 3.3 kbp) was selected in a manner similar to (a) except that pNZ 180 and restriction enzyme EcoR V used in (a) were changed to pNZ 160 and Xba I, respectively. This hybrid plasmid was named pNZ 1004.

(c) Construction of hybrid plasmid (pNZ 1137) having inserted a ligation fragment of vaccinia virus 7.5K promoter and β-galactosidase DNA into EcoR V site of pNZ 136S After digesting pNZ 136S with EcoR V, EcoR I linker (manufactured by Takara Shuzo Co., Ltd.) was linked to the digestion product with ligase. By extraction with phenol-chloroform and precipitation with ethanol, DNA was recovered. After the recovered DNA was likewise digested with EcoR I and Xba I, about 0.2 Kb EcoR I-Xba I fragment was recovered from 1.5% agarose gel. After digesting pNZ 136S with EcoR V, Hind III linker (manufactured by Takara Shuzo Co., Ltd.) was also linked to the digestion product with ligase. By extraction with phenol-chloroform and precipitation with ethanol, DNA was recovered. After the recovered DNA was digested with Hind III and Xba I, about 4.3 Kb Hind III-Xba I fragment was recovered from 0.8% agarose gel. Further after digesting pUC 18 with Hind III and EcoR I, 51 bp fragment of polylinker portion was recovered from 2.0% agarose gel. The about 0.2 Kb EcoR I-Xba I fragment, about 4.3 Kb Hind III-Xba I fragment and 51 bp Hind III-EcoR I fragment thus obtained were ligated with each other by ligase. A plasmid was extracted in a manner similar to Example 1 (4). A plasmid in which 3 fragments had been ligated was detected and this was named pNZ 136SL.

On the other hand, after digesting pNZ 76 with Hind III and Sma I, about 3.6 Kb fragment was recovered in a manner similar to (2). The pNZ 136SL described above was digested with Hind III and Sma I. By extraction with phenol-chloroform and precipitation with ethanol, recovery was performed. Both were ligated with each other by ligase and competent E. coli JM 103 strain was transformed. Subsequently in a manner similar to (2), a hybrid plasmid was selected and this was named pNZ 1137.

(5) Construction of a recombinant Avipoxvirus

Avipoxvirus NP strain was inoculated on chick embryo fibloblasts cultured in a 25 cm² culture flask in 0.05 p.f.u./cell. The hybrid plasmid, 50 μg, obtained in (4) was dissolved in 2.2 ml of sterilized water and, 2.5 ml of a mixture of 1% HEPES (manufactured by GIBCO Co., Ltd.) and 0.6% sodium chloride and 50 μl of buffer solution obtained by mixing 70 mM disodium hydrogenphosphate 12 hydrate and 70 mM disodium hydrogenphosphate 2 hydrate in an equimolar amount were mixed with the solution to prepare an aqueous solution. The aqueous solution was transferred to a 15 ml tube (manufactured by Falcon Co., Ltd.) and 300 μl of 2M calcium chloride aqueous solution was dropwise added thereto while agitating with a stirrer to form DNA-calcium phosphate coprecipitates. Forty five minutes after the inoculation of virus, 0.5 ml of the coprecipitates were dropwise added to the infected chick embryo fibloblasts. After settling in an incubator at 37° C. in 5% CO₂ for 30 minutes, 4.5 ml of Eagle's MEM medium supplemented with 5% bovine fetal serum, 0.03% L-glutamine and 10% Tryptose phosphate broth was added thereto. Three hours after, the culture supernatant was exchanged and cultured in an incubator for 3 days at 37° C. in 5% CO₂. The system including culture cells was frozen and thawed 3 times to give a solution of virus containing recombinant.

(6) Selection of a recombinant by chlorophenol red-β-D-galactopyranoside

The virus solution obtained in (5) was inoculated on chick embryo fibloblasts cultured in a 10 cm Petri dish. Two hours after, 10 ml of phenolred-free Eagle's MEM medium supplemented with 0.8% Bacto agar (manufactured by Difco Co., Ltd.), 5% bovine fetal serum, 0.03% L-glutamine and 10% Tryptose phosphate broth was put thereon in layers followed by incubation in an incubator at 37° C. in 5% CO₂ for 3 days. On the medium was put 10 ml of phenol red-free Eagle's MEM medium supplemented with 0.8% Bacto agar, 0.03% L-glutamine, 10% Tryptose phosphate broth and 0.03% chlorophenol red-β-D-galactopyranoside (Boehringer Mannheim) in layers followed by incubation in an incubator at 37° C. in 5% CO₂ for 6 hours. Recombinant virus expresses β-galactosidase and changes chlorophenol red-β-galactopyranoside to red so that both agar and cells around the recombinant plaque became red and could be easily distinguished over non-recombinant. The recombinant formed from this red plaque was isolated with a sterilized Pasteur pipette. Each recombinant was named as shown in Table 1.

TABLE 1

| Parent Strain | Hybrid Plasmid (C) | Recombinant |
|---|---|---|
| Avipoxvirus NP strain | pNZ 1003 | fNZ 1003 |

TABLE 1-continued

| Parent Strain | Hybrid Plasmid (C) | Recombinant |
|---|---|---|
| Avipoxvirus NP strain | pNZ 1004 | fNZ 1004 |
| Avipoxvirus NP strain | pNZ 1137 | fNZ 1137 |

(7) Analysis of genome DNA of the recombinant Avipoxvirus

After each Avipoxvirus obtained in (6) was subjected to plaque purification, the Avipoxvirus was inoculated on chick embryo fibloblasts cultured in a 10 cm Petri dish in 1 p.f.u./cell. Subsequently in a manner similar to (1), virus DNA was isolated. After 2 μg of each recombinant virus DNA was digested with BamH I or Hind III, fragments were separated by 0.5% agarose electrophoresis (25V, 20 hours). After the DNA was transferred to a nylon membrane by the Southern's method [Journal of Molecular Biology, 98, 503 (1975)], the DNA was immobilized onto the nylon membrane at 80° C. under reduced pressure. After treating with 4-fold SET-[0.6M NaCl, 0.08M Tris HCl (pH 7.8), 4 mM EDTA]-10-fold Denhardt-0.1% SDS at 68° C. for 2 hours, β-galactosidase labelled with $^{32}P$ by nick translation was hybridized with 4-fold SET-10-fold Denhardt-0.1% SDS-modified salmon sperm DNA at 68° C. for 14 hours. After washing and drying, a nylon membrane was put on an X ray film to perform autoradiography, whereby the presence of bands was confirmed. It was confirmed that these recombinant viruses contained the β-galactosidase genes in definite locations.

(8) Identification of non-essential DNA region

From the foregoing results, it will be understood that the EcoR I-Hind III fragment (about 5.0 kbp) used for construction of pNZ 180, BamH I fragment (about 4.0 kbp) used for construction of pNZ 160 and EcoR V-Hind III fragment (about 1.8 kbp) are regions non-essential to proliferation of virus.

In a manner similar to the above, it has also been confirmed that BamH I fragment (about 3.3 kbp) and Hind III fragment (about 5.2 kbp) of DNA from the NP strain are also regions non-essential to proliferation of virus. A restriction enzyme map of these fragments is as shown in FIG. 5.

Furthermore, hybrid plasmids pNZ 1003, pNZ 1004 and pNZ 1137 constructed in (4) all contain the DNA region non-essential to growth of Avipoxvirus and can thus be utilized as a first recombinant vector in the present invention.

EXAMPLE 1

Construction of a second recombinant vector (pNZ 2003) containing HN gene DNA of NDV (cf. FIG. 1)

(1) Construction of hybrid phage (mp10-mpa) containing adaptor:

After digesting 0.1 μg of M13-mp10 RF DNA (manufactured by Amersham Co., Ltd.) with BamH I and Xba I, the digestion product was extracted with phenol and chloroform (1:1). By precipitation with ethanol, cleaved M13-mp10 RF DNA was recovered.

On the other hand, an adaptor composed of 40 bp oligodeoxyribonucleotide having a base sequence described below was chemically synthesized using Genet AIII (manufactured by Nippon Zeon Co., Ltd.). This adaptor was mixed with the cleaved M13-mp10 RF DNA, ligated by ligase and transduced into competent *E. coli* TG-1 strain in a conventional manner (Methods in Enzymology, vol. 101). Incubation was carried out in 2×YT agar medium supplemented with 0.003% 5-bromo-4-chloro-3-indolyl-β-D-galactopyranoside and 0.03 mM isopropyl-β-D-galactopyranoside for 12 hours at 37° C. Among plaques formed, phage RF DNA was recovered from white plaque. This DNA was cleaved with Bgl II. By 0.8% agarose gel electrophoresis, a hybrid phage having inserted therein adaptor DNA was selected and this was named mp10-mpa.

```
       Bgl II                              Xho I
Xba I                            Kpn I                 BamH I
CTAGATCTAAGGAGGAAAAAATTATGGTACCTCGAGCTCG
    TAGATTCCTCCTTTTTTAATACCATGGAGCTCGAGCCTAG
```

(2) Construction of hybrid phage (mp10-HN 115) containing Ava II (about 1.15 kbp) fragment of HN gene DNA of NDV Plasmid XLIII-10H containing NDV HN gene (cf., Virus Research, 7, 241-255 (1987)) was obtained from Assistant Professor Masao Kawakita, of Tokyo University, Department of Liberal Arts. A base sequence of this plasmid was analyzed by the dideoxy method using M13 phage and, it has been clarified by contrasting to the base sequence of known HN gene [J. Gen. Virol., 67, 1917-1927 (1986)] that cDNA of HN gene is 1746 base pairs from 112th to 1857th shown in FIG. 4. This clarification was made by Assistant Professor Kawakita.

The amino acids for which the cDNA obtained herein codes had 90% or more homology to amino acids of HN from the Beaudette strain [N. Miller, J. Gen. Virol., 67, 1917-1927 (1986)] and $B_1$ strain [E. Jorgensen, Virology, 156, 12-24 (1987)].

After digesting 4 μg of plasmid XLIII-10H with Ava II, the digestion product was subjected to 1.5% agarose gel electrophoresis. About 1.15 kbp DNA fragment was extracted from agarose gel and precipitation was carried out with ethanol to recover Ava II fragment of HN gene DNA.

After digesting hybrid phage mp10-mpa RF DNA constructed in (1) with Kpn I, extraction was performed with phenol-chloroform and precipitation with ethanol thereby to recover the cleaved mp10-mpa.

The cleaved mp10-mpa RF DNA, 0.1 μg, was mixed with about 0.2 μg of the Ava II fragment (about 1.15 kbp) of HN gene DNA described above and the cohesive end was made the blunt end by DNA polymerase. After extracting with phenol-chloroform, the DNA was recovered by precipitation with ethanol. The recovered DNA was ligated with ligase and transduced into competent *E. coli* TG-1 strain, which was allowed to grow in 2×YT agar medium at 37° C. for 12 hour. Phage RF DNA was recovered from the formed plaque. After cleaving with Xba I and Xho I, a hybrid phage containing Ava II fragment (about 1.15 kbp) of HN gene DNA was selected by 0.8% agarose electrophoresis. The hybrid phage was named mp10-HN 115 RF.

(3) Construction of hybrid phage (mp10-HN 180) containing HN gene DNA of NDV

Plasmid XLIII-10H, 4 μg, was digested with Aat II and Xho I and about 1.4 kbp Aat II-Xho I fragment of HN gene DNA was recovered in a manner similar to (2).

On the other hand, after hybrid phage mp10-HN 115 RF DNA was digested with Aat II and Xho I, the digestion product was subjected to 0.6% agarose electrophoresis to recover Aat II-Xho I fragment (about 7.7 kbp) of mp10-HN 115.

The Aat II-Xho I fragment (about 7.7 kbp) of HN gene was ligated with the Aat II-Xho I fragment (about 1.4 kbp) of mp10-HN 115 by ligase and phage RF DNA was recovered by operations similar to (2). Phage RF DNA was cleaved with Xho I and Bgl II and, hybrid phage RF DNA containing about 1.8 kbp HN gene DNA fragment was selected by 0.8% agarose electrophoresis, which was named mp10-HN 180 RF.

(4) Construction of a second recombinant vector (pNZ 2003) from the first recombinant vector pNZ 1003 and hybrid phage mp10-HN 180 RF DNA The first recombinant vector pNZ 1003 constructed in Reference 1 (4) was partially digested with BamH I and the product was subjected to 0.6% agarose electrophoresis. Following procedures similar to (2), about 7.6 kbp BamH I fragment was recovered. On the other hand, hybrid phage mp10-HN 180 RF DNA constructed in (3) was digested with BamH I and Bgl II and the product was subjected to 0.8% agarose electrophoresis. Then, BamH I-Bgl II fragment (about 1.8 kbp) containing HN gene DNA was recovered.

The BamH I fragment of about 7.6 kbp obtained by partial digestion of pNZ 1003 with BamH I was mixed with the about 1.8 kbp BamH I-Bgl II fragment containing HN gene DNA. The mixture was ligated with ligase and competent *E. coli* TG-1 strain was transformed, which was allowed to grow on LB agar medium supplemented with 40 μg/ml of ampicillin at 37° C. for 15 hours. A plasmid was recovered from the grown *E. coli* in a manner similar to Reference Example 1 (2). The plasmid was digested with BamH I and a recombinant vector containing a fragment (about 3.1 kbp) having ligated therewith 7.5k promoter and HN gene was selected by 0.8% agarose electrophoresis. This vector was named pNZ 2003.

pNZ 2003 corresponds to a second recombinant vector in the present invention.

EXAMPLE 2

Construction of a second recombinant vector (pNZ 2104) containing NDV HN gene DNA (cf. FIG. 2)

(1) Construction of hybrid plasmid pHN 18 from hybrid phage mp10-HN 180 RF DNA pUC 18 was digested with BamH I. After extraction with phenol-chloroform, cleaved pUC 18 was recovered by precipitation with ethanol. This fragment and the about 1.8 kbp BamH I-Bgl II fragment containing HN gene DNA obtained in Example 1 (4) were ligated by ligase and competent *E. coli* TG-1 strain was transformed. A plasmid was extracted in a manner similar to Reference Example 1 (2). After digesting with BamH I and Xba I, a hybrid plasmid containing HN gene was detected by 0.8% agarose electrophoresis and this was named pHN 18.

(2) Construction of a second recombinant vector (pNZ 2104) from the first recombinant vector pNZ 1004 and hybrid plasmid pHN 18

The first recombinant vector pNZ 1004 constructed in Reference 1 (4) was digested with EcoR I and the product was subjected to 0.6% agarose electrophoresis, whereby about 6.2 kbp DNA fragment and about 3.5 kbp DNA fragment were independently recovered. After the about 6.2 kbp EcoR I fragment was digested with EcoR V and further partially digested with Xba I, the digestion product was subjected to 0.8% agarose electrophoresis to recover about 3.3 kbp Xba I-EcoR I fragment containing 7.5k promoter. Further the 3.5 kbp EcoR I fragment was further digested with BamH I and then subjected to 0.8% agarose electrophoresis to recover BamH I-EcoR I fragment of about 3.3 kbp.

On the other hand, hybrid plasmid pHN 18 constructed in (1) was digested with BamH I and then partially digested with Xba I. The digestion product was subjected to 0.8% agarose electrophoresis to recover BamH I-Xba I fragment containing HN gene DNA (about 1.8 kbp). The about 3.3 kbp Xba I-EcoR I fragment obtained from pNZ 1004 described above, the about 3.3 kbp Xba I-EcoR I fragment and the about 1.8 kbp BamH I-Xba I fragment containing HN gene DNA were mixed and ligated by ligase. In a manner similar to Example 1 (4), a recombinant vector containing a fragment (about 2.1 kbp) having ligated therewith 7.5k promoter and HN gene was selected and named pNZ 2104. pNZ 2104 corresponds to a second recombinant vector in the present invention.

EXAMPLE 3

Figure 3A:
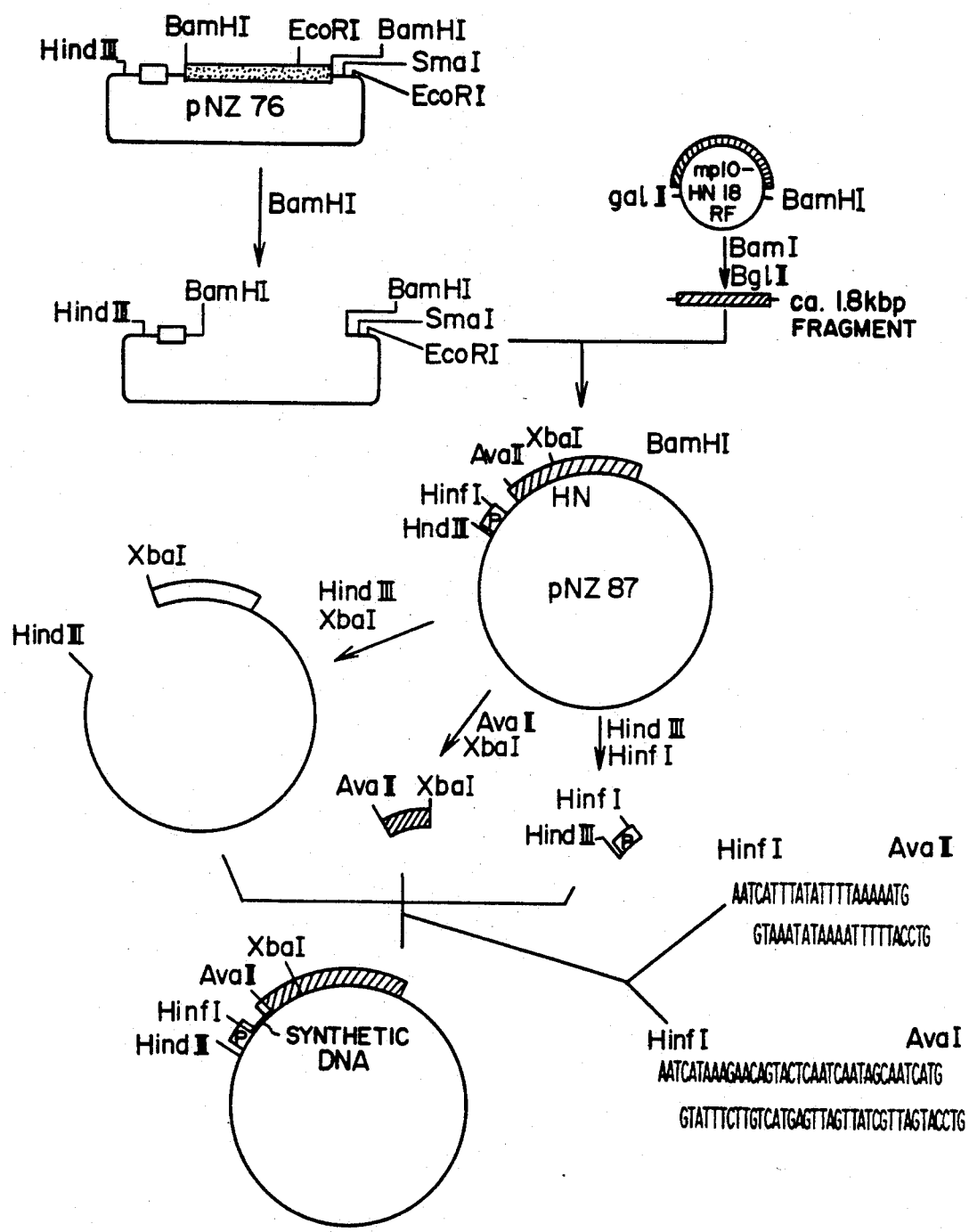
Figure 3B:
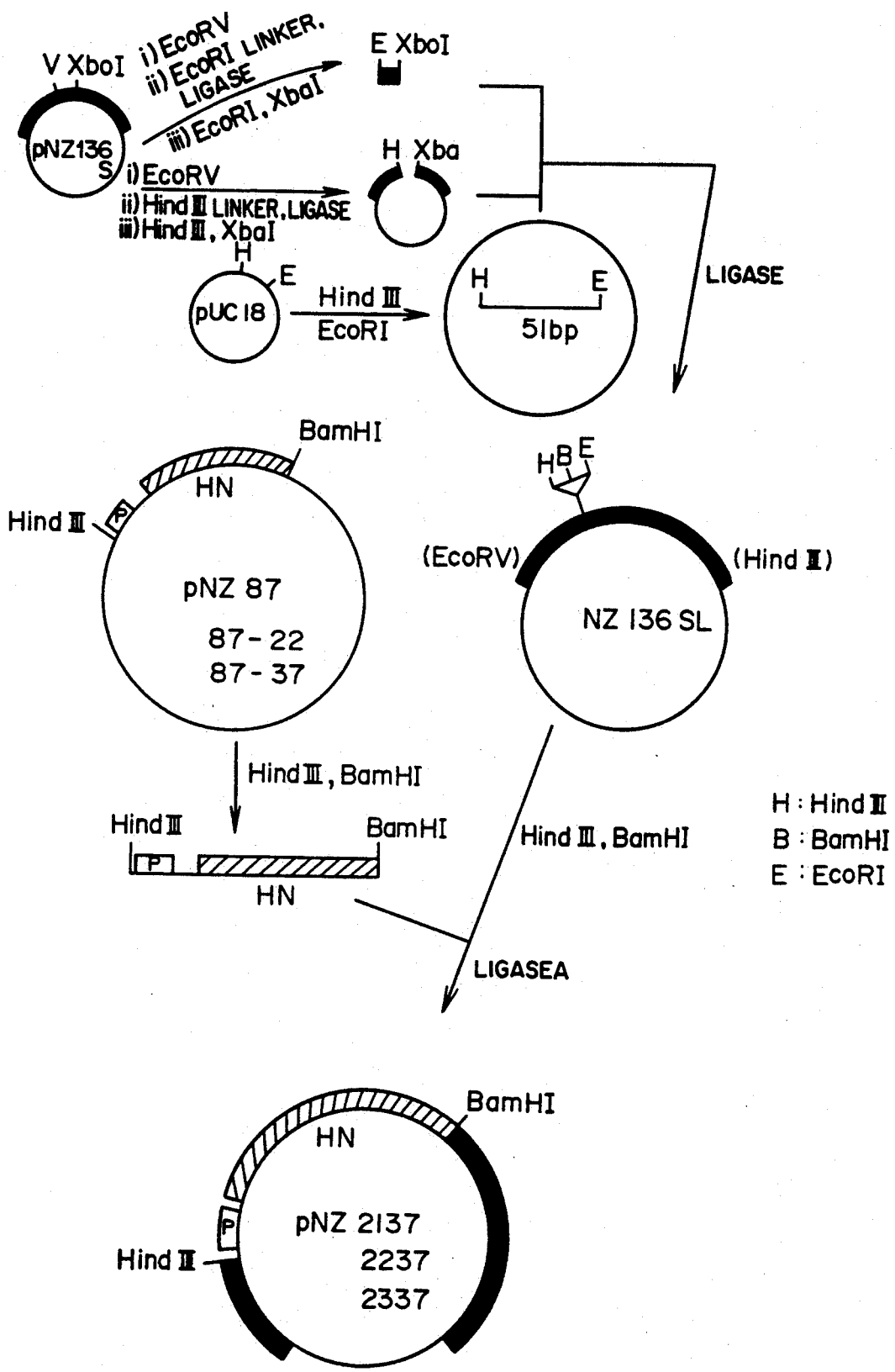
Figure 5A:
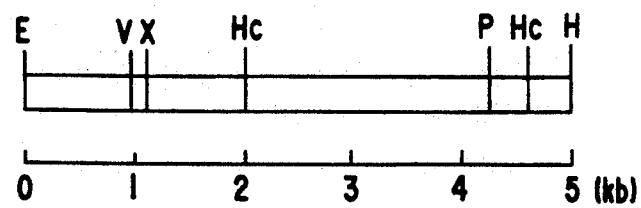
FIG. 5 shows an example of a DNA region non-essential to proliferation of Avipoxvirus.
Figure 5B:
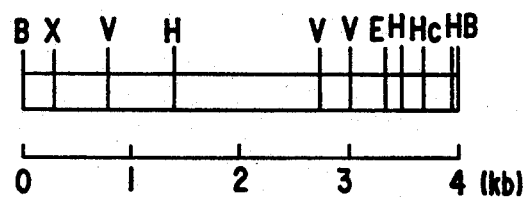
Figure 5C:
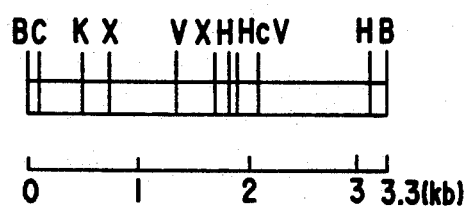
Figure 5D:
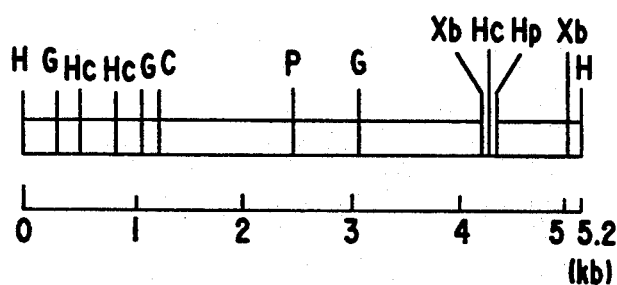
Figure 5E:
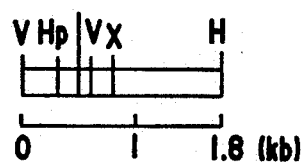

Construction of second recombinant vectors (pNZ 2137, pNZ 2237 and pNZ 2337) containing NDV HN gene DNA (cf. FIG. 3)

(1) Construction of hybrid plasmid pNZ 87 having ligated therewith a promoter and NDV HN gene DNA under its control, from hybrid phage mp10-HN 180 pNZ 76 was digested with BamH I and about 2.9 kb fragment free from β-galactosidase gene was recovered from 0.8% agarose gel. On the other hand, hybrid phage mp10-HN 180 was digested with Bgl II and BamH I and NDV HN gene DNA fragment was then recovered from 0.8% agarose gel. Both were ligated by ligase and competent *E. coli* TG-1 was transformed. A plasmid was extracted and a hybrid plasmid containing HN gene was detected in a manner similar to Reference Example 1 (2). This was named pNZ 87.

(2) Construction of vaccinia virus 7.5 k promoter-bearing plasmids (pNZ 87-22 and pNZ 87-37) in which base sequence of HN gene up to translation initiation sequence has been changed pNZ 87 was digested with Xba I and Hind III to recover about 4.3 kb of Xba I-Hind III fragment (fragment (1)). Likewise, pNZ 87 was digested with Xba I and Ava II to recover about 0.2 kb of Xba I-Ava II fragment (fragment (2)). Further pNZ 87 was digested with Hind III and Hinf I to recover about 0.2 kb of Hind III-Hinf I fragment (fragment (3)). To the fragments (1), (2) and (3) obtained herein was added synthetic DNA (4) (22 bp) shown below:

```
Hinf I                              Ava II
     AATCATTTATATTTTAAAAATG
         GTAAATATAAAATTTTTACCTG
``` or synthetic DNA (5) (37 bp) shown below:

```
Hinf I                                            Ava II
    AATCATAAAGAACAGTACTCAATCAATAGCAATCATG
        GTATTTCTTGTCATGAGTTAGTTATCGTTAGTACCTG
``` followed by ligation with ligase. Plasmids were extracted in a manner similar to Example 1 (4) and hybrid plasmids containing synthetic DNA (4) and (5), respectively, were detected. These plasmids were named pNZ 87-22 and pNZ 87-37.

(3) Construction of second recombinant vectors (pNZ 2137, pNZ 2237 and pNZ 2337) from hybrid plasmids pNZ 87, pNZ 87-22 and pNZ 87-37 having ligated therewith pNZ 136SL corresponding to hybrid plasmid (A), promoter and HN gene DNA under control of the promoter Hybrid plasmid pNZ 136SL constructed in Reference Example 1 (2)-(c) was digested with Hind III and BamH I. After extraction with phenol-chloroform, recovery was performed by precipitation with ethanol. On the other hand, after pNZ 87, pNZ 87-22 and pNZ 87-37 were digested with Hind III and BamH I, respectively, the digestion products were subjected to 0.8% agarose electrophoresis to recover about 2.1 kb Hind III-BamH I fragment containing vaccinia virus 7.5k promoter and HN gene DNA. The former was ligated with each of the latter using ligase. Recombinant vectors bearing a fragment (about 2.1 kb) having ligated therewith 7.5k promoter and HN gene were selected and named pNZ 2137, pNZ 2237 and pNZ 2337, respectively. They correspond to a second recombinant vector in the present invention.

EXAMPLE 4

Construction of a recombinant Avipoxvirus containing NDV HN gene

A solution of recombinant Avipoxvirus containing NDV HN gene was obtained in a manner similar to Reference Example 1 (5) except that the second recombinant vectors obtained in Examples 1, 2 and 3 were used in place of the hybrid plasmid used in Reference Example 1 (5).

EXAMPLE 5

Selection of recombinant by plaque hybridization

The virus solution obtained in Example 4 was inoculated on chick embryo fibloblasts cultured in a 10 cm Petri dish. Two hours after, 10 ml of Eagle's MEM medium supplemented with 0.8% Bacto agar, 5% bovine fetal serum, 0.03% L-glutamine and 10% Tryptose phosphate broth was overlaid in layers followed by incubation in an incubator at 37° C. in 5% $CO_2$ for 3 days. On the medium was further overlaid in layers 10 ml of Eagle's MEM medium having the same composition as described above followed by incubation in an incubator at 37° C. in 5% $CO_2$ for 3 days. Further 10 ml of Eagle's MEM medium supplemented with 0.8% Bacto agar, 0.03% L-glutamine, 10% Tryptose phosphate broth and 0.01% of neutral red was overlaid in layers followed by incubation in an incubator at 37° C. in 5% $CO_2$ for 12 hours to stain infected cells.

The agar medium was withdrawn from the Petri dish. A sterilized nylon membrane was pushed onto the surface of cells kept at 4° C. and remained on the bottom of the Petri dish to transfer the viruses thereon. After repeating a treatment with 0.5N NaOH for 10 minutes and with 1M Tris-hydrochloride buffer for 5 minutes 3 times, the system was treated with 1.5M NaCl and 0.5M Tris-hydrochloride buffer for 5 minutes. The system was saturated with 2-fold SSC [1-fold SSC, 0.15M NaCl, 0.015M $C_3H_4(OH)(COONa)_3$] and sintered at 80° C. for 2 hours. The system was treated with 4-fold SET (0.6M NaCl, 0.08M Tris HCl, 4 mM EDTA, pH 7.8)-10-fold Denhardt-0.1% SDS at 68° C. for 2 hours. 4-Fold SET-10-fold Denhardt-0.1% SDS-0.1% $Na_4P_2O_7$-50 μg/ml-modified salmon sperm DNA and cDNA coding for HN of NDV labeled with $^{32}P$ were hybridized by nick translation at 68° C. for 14 hours. After washing, the nylon membrane was put on an X ray film, which was subjected to autoradiography to confirm the presence of a spot. The X ray film was overlaid on the agar kept at 4° C. and a plaque coincided with the spot was identified to be a recombinant containing HN gene. The recombinant was isolated with a sterilized Pasteur pipette. Two plaques of this recombinant appeared per 10 Petri dishes of 10 cm in which approximately 500 plaques appeared (about 0.04%).

With respect to the thus obtained recombinant viruses, a recombinant virus obtained using pNZ 2003 was named fNZ 2003. Likewise, those obtained using pNZ 2104, pNZ 2137, pNZ 2237 and pNZ 2337 were named fNZ 2104, fNZ 2137, fNZ 2237 and fNZ 2337, respectively.

EXAMPLE 6

Purification of recombinant Avipoxvirus containing NDV HN gene

The plaque isolated in Example 5 was suspended in 1 ml of Eagle's MEM and 200 μl of the suspension was inoculated on chick embryo fibloblasts cultured in a 10 cm Petri dish. Two hours after, 10 ml of phenol red-free Eagle's MEM medium supplemented with 0.8% Bacto agar, 5% bovine fetal serum, 0.03% L-glutamine and 10% Tryptose phosphate broth was overlaid thereon in layers followed by incubation in an incubator at 37° C. in 5% $CO_2$ for 3 days. On the medium was overlaid in layers 10 ml of phenol red-free Eagle's MEM medium having the same composition described above followed by incubation in an incubator at 37° C. in 5% $CO_2$ for 3 days. On the medium was overlaid in layers 10 ml of phenol red-free Eagle's MEM medium supplemented with 0.8% Bacto agar, 0.03% L-glutamine and 10% Tryptose phosphate broth followed by incubation in an incubator at 37° C. in 5% $CO_2$ for 6 hours. The recombinant plaque formed a spot on an X ray film as in Example 5.

The foregoing operations were repeated in a similar manner to again purify the recombinant.

As a result, 20 recombinant plaques (red plaque) (0.2%) appeared with fNZ 1004, per 10 Petri dishes of 10 cm in which approximately 500 plaques per dish appeared in Example 5; in the first plaque purification, 90 (15%) of the recombinant plaques appeared in 3 Petri dishes in which about 200 plaques per dish appeared. In the second plaque purification, almost all plaques were recombinants. Also with respect to fNZ 2104, fNZ 2137, fNZ 237 and fNZ 2337, almost the same results were obtained.

EXAMPLE 7

Expression of recombinant in cell (fluorescent antibody technique)

Virus strains (fNZ 2003, fNZ 2104, fNZ 2137, fNZ 2237 and fNZ 2337) of the present invention showing m.o.i of 1.0 or 0.1 were inoculated on chick embryo fibloblasts cultured in a 5% $CO_2$ incubator for 2 hours, Eagle's MEM medium supplemented with 10% Tryptose phosphate broth (Difco Co., Ltd.) and 0.03% L-glutamine was added. Thereafter, incubation was performed for 2 days at 37° C. in a 5% $CO_2$ incubator and the medium was then withdrawn. After washing with PBS (phosphate buffered saline) and air drying, the system was treated with acetone at −20° C. for 20 minutes to immobilise the cells. By examining in accordance with fluorescent antibody technique using as a primary antibody anti-NDV chick antibody and as a secondary antibody fluorescein isocyanate-bound anti-chick IgG antibody, it was confirmed that the recombinant Avipoxviruses had NDV HN protein productivity.

EXAMPLE 8

Expression of recombinant in cell (enzyme antibody technique)

The virus solution obtained in Example 6 was inoculated on chick embryo fibloblasts cultured in a 10 cm Petri dish. Two hours after, 10 ml of Eagle's MEM medium supplemented with 0.8% Bacto agar, 5% bovine fetal serum, 0.03% L-glutamine and 10% Tryptose phosphate broth was overlaid in layers followed by incubation in an incubator at 37° C. in 5% $CO_2$ for 3 days. Furthermore, 10 ml of Eagle's MEM having the same composition as described above was overlaid in layers followed by incubation in an incubator at 37° C. in 5% $CO_2$ for 3 days.

The agar medium was withdrawn from the Petri dish. A sterilized nylon membrane was pushed onto the surface of cells remained on the bottom of the Petri dish to transfer virus plaques and cells thereon. After treating with PBS (phosphate buffered saline) containing 2% skimmed milk for 30 minutes, anti-NDV chick antibody was reacted as a primary antibody at room temperature for an hour. After the reaction, the mixture was washed with PBS and biotinated anti-chick IgG antibody was reacted as a secondary antibody at room temperature for an hour. After the reaction, the mixture was washed with PBS and horse radish peroxidase-bound avidin-biotin complex was reacted at room temperature for 30 minutes. After the reaction, a color was formed with 8 mM Tris-hydrochloride buffer (pH 8.0) containing 0.05% 4-chloro-1-naphthol and 0.3% $H_2O_2$. By checking with the foregoing enzyme antibody method, it was confirmed that the recombinant Avipoxviruses had NDV HN protein productivity.

EXAMPLE 9

Recombinant virus strain fNZ2237 was cultured in chick embryo fibroblast (CEF) in five flasks (150 cm²/flask) at 37° C. for 48 hours. After recombinant virus propagated-CEF was subjected to freeze-thawing twice, a cell suspension was collected and centrifuged at 2,000 rpm for 15 minutes. To 130 ml of the supernatant were added 40 ml of 20 %(v/v) sodium glutamate solution and 30 ml of 10 %(v/v) saccharose solution. The mixture was put into 100 vials by 2 ml each. After preliminary freezing for 1.5 hours, freeze-drying was conducted for 30 hours under reduced pressure. One vial of vaccine was dissolved in 10 ml of physiological saline supplemented with 30 %(v/v) glycerol, and 0.01 ml/chick of the solution was inoculated into the right wing web of 7-day-old specific pathogen free (SPF) chick by the stick method. After inoculation, vaccination rash of chick was observed. At 2 weeks post-vaccination hemagglutination-inhibition (HI) antibody of Newcastle disease virus (NDV) was measured. Virulent NDV Sato strain and virulent fowlpox virus Nishigahara strain were challenged at 2 and 3 weeks post-vaccination respectively, whereby an immune effect of the vaccine was determined.

HI test of NDV was performed as described below. Twenty-five μl of NDV hemagglutination (HA) antigen containing 4 HA units were added to an equal volume of 2-fold serial serum dilution in microtiter plate. The plate were allowed to stand at room temperature for 10 minutes followed by mixing. Then 50 μl of 0.5 %(v/v) chicken red blood cell suspension was added to each well and the mixture was allowed to stand at room temperature for 45 minutes. HI titer was determined as the reciprocal of the highest dilution showing complete inhibition.

Effects of the vaccine are shown in Table 2. In the chick inoculated with the recombinant vaccine of the present invention, occurrence of skin swelling, that showed the reaction of chick with fowlpox virus vaccine, was noted as in ordinary fowlpox virus vaccine and no eruption was observed followed by challenge of fowlpox virus virulent strain at 3 weeks postvaccination. Furthermore, HI antibody of chick to NDV was detected and chick was resistant to challenge of virulent NDV strain at 2 weeks post-vaccination.

From these results, it is shown that the recombinant vaccine of the present invention is capable of immunizing chicks against fowlpox and NDV infection at the same time.

TABLE 2

| Group | Chick No. | State of Fowlpox | ND-HI Titer 2 Weeks | 3 Weeks | Challenge* FPV | NDV |
|---|---|---|---|---|---|---|
| Vaccinated group | 1 | take | 1:64 | 1:256 | − | − |
| | 2 | " | 1:128 | 1:64 | − | − |
| | 3 | " | 1:16 | 1:32 | − | + |
| | 4 | " | 1:16 | 1:64 | − | − |
| | 5 | " | 1:16 | 1:64 | − | − |
| Intact control group | 1 | no pox | <1:2 | <1:2 | + | + |
| | 2 | " | <1:2 | <1:2 | + | + |
| | 3 | " | <1:2 | <1:2 | + | + |
| | 4 | " | <1:2 | <1:2 | + | + |
| | 5 | " | <1:2 | <1:2 | + | + |

*FPV +: Eruption is noted.
(3 weeks) −: No eruption is noted.
NDV +: Symptoms and death are noted.
(2 weeks) −: Resistance to challenge is noted.

EXAMPLE 10

Each vaccine solution prepared by culturing recombinant virus strains fNZ2237 in the same manner as in Example 9 was inoculated into chicks. After 2 weeks, HI titers of respective vaccinated chicks were determined in addition to the gross observation of their growth. Thereafter, the respective chicks were challenged with virulent NDV Sato strain. Two weeks after the challenge, the HI titer of each chick was determined. The rate of survival of the chicks was also determined to evaluate the protection activity against the challenge (the survival rate).

The chicks for control were treated in the same manner as those vaccinated including challenge with virus except that the chicks were not inoculated with recombinant virus, and were housed in the same cage as that for the treated ones.

The results are shown in Table 3.

TABLE 3

| Group | No. of chicks employed | Gross observation | Relative body weight (1) 2 weeks after inoculation | HI titer (2) | | Survival rate 2 weeks after challenge |
| --- | --- | --- | --- | --- | --- | --- |
| chicks inoculated with fNZ2237 | 34 | Fowl pox taken | 0.84 | 1:15 | 1:135 | 80% |
| chicks inoculated with fNZ2237 | 5 | Fowl pox taken | 1.09 | 1:37 | 1:263 | 100% |
| control (not inoculated) | 5 | none | — | <1:2 | — | 0% |

Notes:
(1) calculated taking the body weight of the control chicks as 1.00
(2) given in the geometrical mean of the HI titers of chicks surviving at the time of the determination.

What is claimed is:

1. A recombinant Nanako dovepoxvirus having inserted therein a promoter operably linked to a nucleotide sequence consisting essentially of a full-length cDNA coding for Newcastle Disease Virus hemagglutinin neuraminidase into a genomic region non-essential to the proliferation of the Nanako dovepoxvirus.

2. A recombinant Avipoxvirus which induces a protective immune response in domesticated fowl again Newcastle Disease, said Avipoxvirus having inserted therein a nucleotide sequence consisting essentially of a promoter operably linked to a Newcastle Disease Virus hemagglutinin neuraminidase cDNA, wherein said cDNA encodes the amino acid sequence as shown in FIG. 4, said insertion being into a genomic region which is nonessential for proliferation of Avipoxvirus.

3. A recombinant Avipoxvirus according to claim 2, wherein said cDNA has a base sequence represented in FIG. 4 and said genomic region non-essential to proliferation of Avipoxvirus is capable of homologous recombination with an approximately 5.0 kbp EcoRI-Hind III fragment, with an approximately 4.0 kbp BamHI fragment, with an approximately 1.8 kbp Eco RV-Hind III fragment, with an approximately 3.3 kbp BamHI fragment, or with an approximately 5.2 kbp HindIII fragment of the DNA of a chick embryo habituated dovepoxvirus Nakano strain.

4. A recombinant Avipoxvirus according to claim 2, wherein said cDNA is operably linked to the vaccinia virus 7.5k promoter.

5. A recombinant Avipoxvirus according to claim 4, wherein said genomic region non-essential to proliferation of Avipoxvirus is capable of homologous recombination with an approximately 5.0 kbp EcoRI-HindIII fragment, an approximately 4.0 kbp BamHI fragment, an approximately 1.8 kbp EcoRV-HindIII fragment, an approximately 3.3 kbp BamHI fragment, or an approximately 5.2 kbp HindIII fragment of DNA of a chick embryo habituated dovepoxvirus Nakano strain.

6. A vaccine for fowl which induces an anti-viral immunity against fowlpoxvirus and Newcastle Disease Virus, which comprises the recombinant Avipoxvirus according to any one of claims 4, 5 or 2.

7. A vaccine for chickens which induces an anti-viral immunity against fowlpoxvirus and Newcastle Disease Virus, consisting essentially of the recombinant Avipoxvirus according to any one of claims 4, 5 or 2.

* * * * *

UNITED STATES PATENT AND TRADEMARK OFFICE
CERTIFICATE OF CORRECTION

PATENT NO.   : 5,286,639
DATED        : February 15, 1994
INVENTOR(S)  : YANAGIDA et al.

It is certified that error appears in the above-identified patent and that said Letters Patent is hereby corrected as shown below:

On the cover page, Item [73], please correct the assignee to show joint assignees as follows: --Nippon Zeon Co., Ltd., Tokyo, Japan; and Shionogi & Co., LTD., Osaka-shi, Japan--.

Signed and Sealed this

Twenty-fifth Day of October, 1994

*Attest:*

*Attesting Officer*

BRUCE LEHMAN

*Commissioner of Patents and Trademarks*